US006971067B1

United States Patent
Karson et al.

(10) Patent No.: US 6,971,067 B1
(45) Date of Patent: Nov. 29, 2005

(54) APPLICATION LAUNCHPAD

(75) Inventors: Tom Karson, Jamaica Plains, MA (US); David Fusari, Groton, MA (US); Gail Fitzpatrick, Carlisle, MA (US); Elaine Seliger, Winchester, MA (US)

(73) Assignee: Sentillion, Inc., Andover, MA (US)

( * ) Notice: Subject to any disclaimer, the term of this patent is extended or adjusted under 35 U.S.C. 154(b) by 464 days.

(21) Appl. No.: 09/645,051

(22) Filed: Aug. 23, 2000

Related U.S. Application Data

(60) Provisional application No. 60/150,269, filed on Aug. 23, 1999.

(51) Int. Cl.[7] .................................................. G06F 3/00
(52) U.S. Cl. ........................ 715/777; 715/778; 715/779; 715/780; 715/789; 705/2
(58) Field of Search .................................. 345/711, 712, 345/717, 733, 734, 736–743, 746, 748, 760, 763, 781, 784, 786, 777, 787, 837, 847; 709/202, 203, 217, 219, 229; 715/777, 778, 784, 787, 837, 845, 847, 779, 780, 789; 705/2, 3

(56) References Cited

U.S. PATENT DOCUMENTS

| | | | | |
|---|---|---|---|---|
| 5,619,639 A | | 4/1997 | Mast ........................... | 395/326 |
| 5,634,095 A | * | 5/1997 | Wang et al. ................. | 345/763 |
| 5,761,669 A | * | 6/1998 | Montague et al. ......... | 707/103 R |
| 5,864,664 A | * | 1/1999 | Capps et al. ................ | 713/200 |
| 5,935,251 A | | 8/1999 | Moore ......................... | 713/202 |
| 5,991,807 A | * | 11/1999 | Schmidt et al. ............. | 709/225 |
| 6,144,991 A | * | 11/2000 | England ...................... | 709/205 |
| 6,175,363 B1 | * | 1/2001 | Williams et al. ............ | 345/746 |
| 6,313,854 B1 | * | 11/2001 | Gibson ........................ | 345/788 |
| 6,327,628 B1 | * | 12/2001 | Anuff et al. ................. | 719/311 |
| 6,331,858 B2 | * | 12/2001 | Fisher ......................... | 345/582 |
| 6,339,826 B2 | * | 1/2002 | Hayes et al. ................ | 709/226 |
| 6,401,138 B1 | | 6/2002 | Judge et al. | |
| 6,476,833 B1 | * | 11/2002 | Moshfeghi ................... | 345/854 |
| 6,567,801 B1 | * | 5/2003 | Chiang et al. ................ | 707/3 |

OTHER PUBLICATIONS

Alan Simpson, "Windows 95 Uncut," IDG Books, ©1997, pp. 30–40.*

Richter, J., *Advanced Windows 3rd Edison*, Microsoft Press, 1997, pp. 905–911.

Stardock Systems, Inc., "Object Desktop Professional User's Guide", XP002154063, (1996).

* cited by examiner

*Primary Examiner*—Ba Huynh
*Assistant Examiner*—Truc T Chuong
(74) *Attorney, Agent, or Firm*—Wolf, Greenfield & Sacks, P.C.

(57) ABSTRACT

A software program provides a unified, ever-present user interface which manages a user's interaction with other software programs. The software program includes an executable portion and a dynamic linked library (DLL). The software program uses hooking and subclassing in a Windows environment to gain control over when and where display of the user interface occurs.

23 Claims, 4 Drawing Sheets

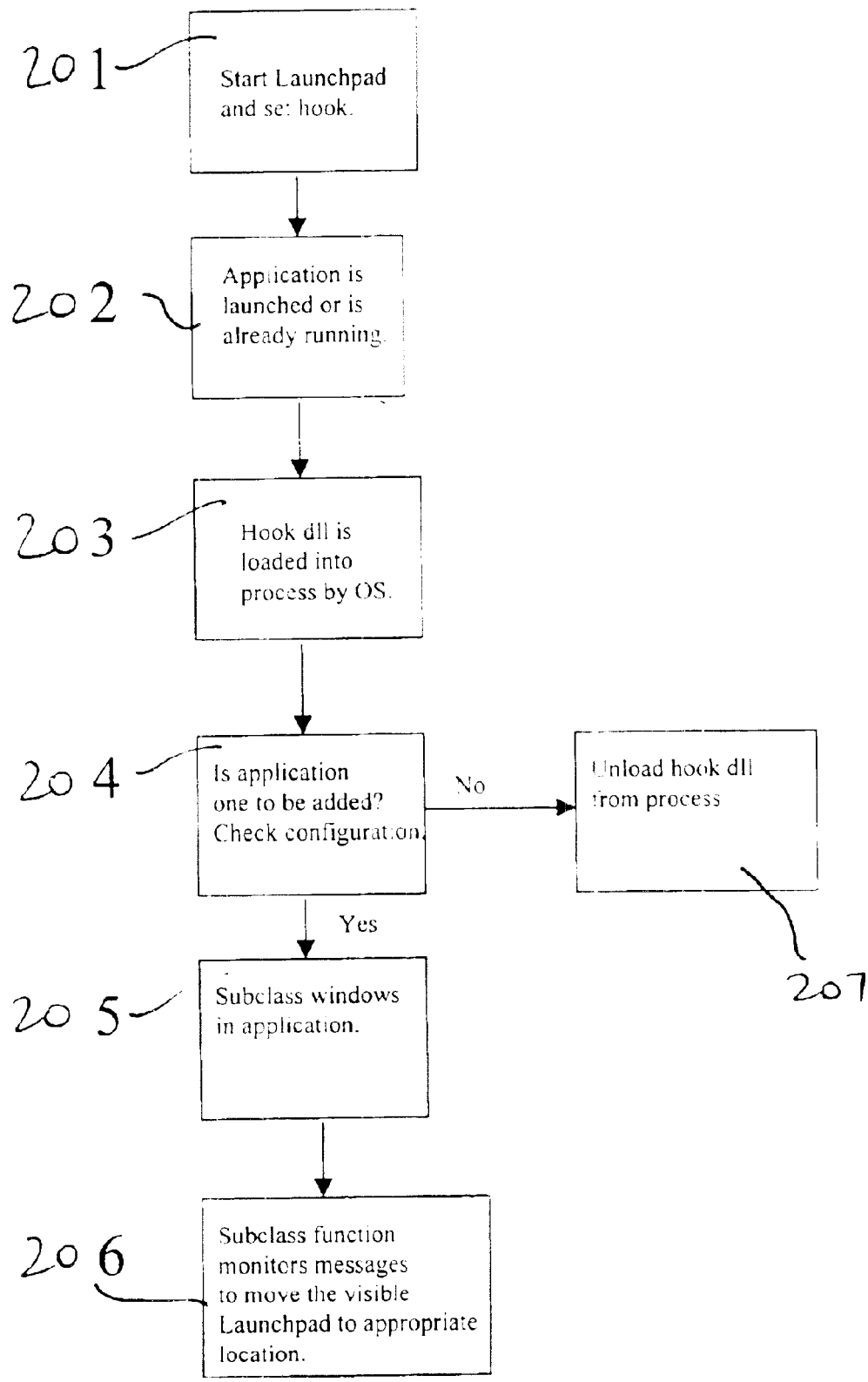

Figure #3
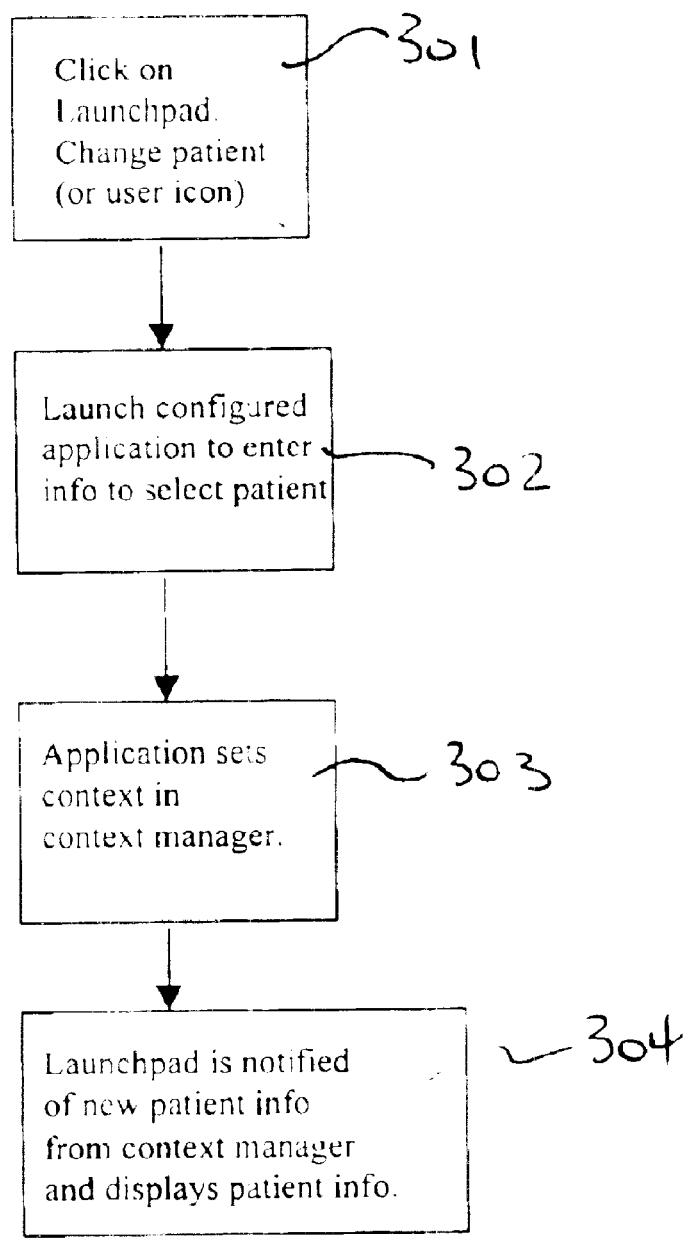

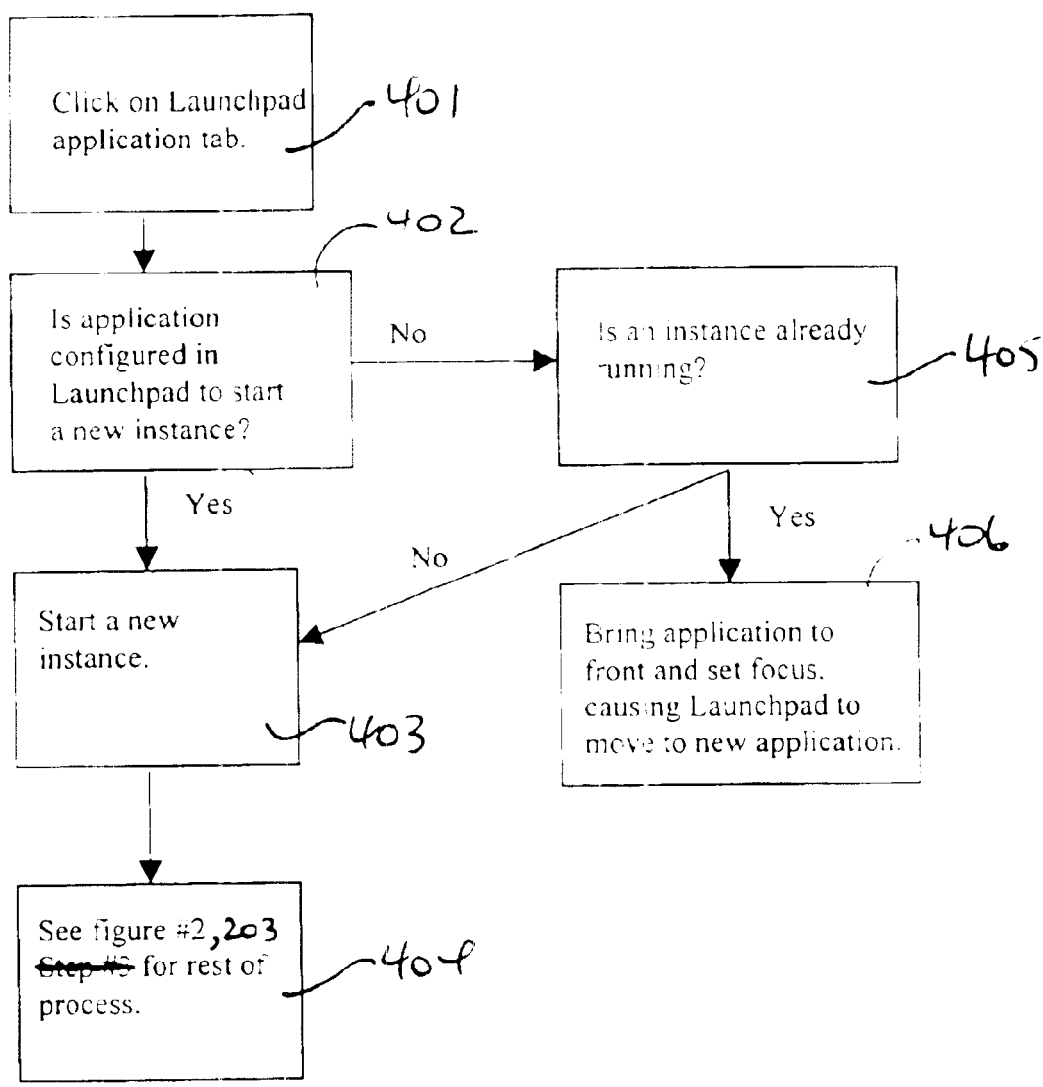
Figure #4

APPLICATION LAUNCHPAD

CROSS-REFERENCE TO RELATED APPLICATIONS

This application claims the benefit under 35 U.S.C. §119 (e) of the filing date of U.S. Provisional Application Ser. No. 60/150,269, entitled "APPLICATION LAUNCH PAD", filed Aug. 23, 1999.

BACKGROUND OF THE INVENTION

1. Field of the Invention

The present invention relates to a software program providing a user interface for management of a user's interaction with other software programs.

2. Related Art

There are many businesses or fields of endeavor, which rely on the use of plural desktop computer applications. One such field is the modem practice of medicine. In such a setting, users quite often find themselves entering and reentering similar information over and over. For example, a single user may have to repeat login information in plural applications, followed by the same or similar client information. Such information, that defines the environment in which each application operates is known as context. That is, context is a collection of data items and corresponding values, wherein the items represent information required in common between plural applications in an industry or business setting. For example, in health care, a patient identifier (patient ID) is an item which is part of the context in which plural clinical applications may participate, or share.

In the modem practice of medicine, a physician or other professional or staff member may need to store, retrieve, analyze, etc. various types of patient data. The patient data to be processed may be clinical; e.g. x-ray images or blood work results, or may be financial, e.g. insurance cover and billing history. Thus, clinical applications, such as those to store, retrieve and display x-ray images and those to store, retrieve and display blood work results have inputs and outputs which fall into two broad classes: highly specialized, work product specific I/O; and more general, context-related I/O.

The desirability of managing context information, so that a user at a workstation need not reenter information such as user identification (user ID) or patient identification (patient ID) has long been recognized.

A standard known as Health Level Seven Context Management Specification Version CM-1.1 was promulgated by the Health Level Seven (HL7) Clinical Context Object Workgroup (CCOW) on Nov. 6, 1999, incorporated herein in its entirety by reference, to define an interface and other architectural definitions of a Context Management Architecture (CMA), whereby clinical applications interact with a Context Manager to manage context information across a range of clinical and other health care related applications.

At this time, there are no other known, comprehensive context management software packages available. Some small steps have been taken for example to share context amongst one publisher's own titles, using proprietary methods absent a context manager, or to permit a user to sign onto a single application which transfers user context to plural other applications. However, no context manager handling both user and patient context is known, much less a complete system with central administration of the context management process.

Conventionally, context management of context enabled applications is a distributed process. Context enabled software, compliant with industry standards, transfer changes in context automatically from one to another. For example, in the healthcare industry, a single workstation may be executing several clinical applications at once. If those applications are context enabled, then when a user changes context information, such as the patient identification in one application, then that context information is transferred by the context management system to the other clinical applications, as explained above. However, conventional context management software is not directly accessed by users. Rather, users make entries and changes through the managed applications. Changes to context information made in context-enabled applications are then transferred automatically by the context management software to other context-enabled applications.

Oversight of context management software can be performed by a context administrator software program. Such a program brings certain administrative functions under centralized control. However, information services personnel usually administer and maintain these systems. Thus, context administration does not fundamentally change the way in which users interact with context-enabled software. Context administration can oversee such functions as which context-enabled applications on a particular workstation are part of a common context and which are not.

Many of the concepts employed in conventional context management and context administration systems are described in U.S. Provisional Patent Applications Ser. Nos. 60/128,145, 60/135,907, 60/136,670, 60/139,235, 60/146,722 and 60/145,681, all incorporated herein by reference. Some of these concepts are further described in U.S. patent application Ser. Nos. 09/545,396 and 09/583,301, also incorporated herein by reference.

One area which has conventionally been problematic in this field of art has been that of user interfaces. Conventionally, there has been no uniform approach to launching, using and context managing plural applications from the standpoint of individual users.

SUMMARY OF THE INVENTION

What is desired is to provide an improved user interface for context management.

According to some embodiments of the invention, a software program stored on a computer-readable medium, can include computer instructions which when executed by a computer cause the computer to execute a sequence of steps comprising identifying a user interface element of a process having a focus, the process executing on the computer attaching to the user interface element of the process a user interface element of the software program moving and resizing the user interface element of the software program together with the user interface element of the process, so the user interface element of the software program and the user interface element of the process together give an impression of one user interface. In one variation, the sequence of steps can also include displaying a control for a user to enter context information used by one or more context managed application programs. In another variation the sequence of steps can include displaying a control which when activated displays context information. In yet another variation, the sequence of steps can include displaying a scrollable set of tabs representing applications which can be launched. The sequence of steps can further include defining a set of applications assigned to the scrollable set of tabs. In other variations, the sequence of steps can include displaying a control which when activated, invokes an instantiation of a web browser pointed to a predetermined web site. In such a variation, the sequence of steps can include defining the predetermined web site or defining a visual image for the control which invokes the web browser including a corporate logo. In yet another variation, the software program can include defining controls on the user interface element dependent on an identified user. Defining controls can further include displaying a scrollable set of tabs representing applications which the identified user has permission to launch. Defining controls can also including displaying a set of controls defined for the identified user at a particular workstation.

The present invention can also be practices as a method of controlling a computer comprising steps of identifying a user interface element of a process having a focus, the process executing on the computer attaching to the user interface element of the process a user interface element of the software program moving and resizing the user interface element of the software program together with the user interface element of the process, so the user interface element of the software program and the user interface element of the process together give an impression of one user interface. Additionally, according to various variations, the steps may include one or more of displaying a control for a user to enter context information used by one or more context managed application programs, displaying a control which when activated displays context information or displaying a scrollable set of tabs representing applications which can be launched. In addition, the method may include defining a set of applications assigned to the scrollable set of tabs. According to another variation, the method may include displaying a control which when activated, invokes an instantiation of a web browser pointed to a predetermined web site. In such a variation, further variations may include defining the predetermined web site or defining a visual image for the control which invokes the web browser including a corporate logo. In yet other variations, the method may include defining controls on the user interface element dependent on an identified user which may itself include displaying a scrollable set of tabs representing applications which the identified user has permission to launch or displaying a set of controls defined for the identified user at a particular workstation.

BRIEF DESCRIPTION OF THE DRAWINGS

In the figures, in which like reference designations indicate like elements:

FIG. 2 is a flowchart of a process of establishing and maintaining a user interface window visually attached to an existing windows process window;

FIG. 3 is a flowchart of a process of managing context information from a common user interface; and FIG. 4 is a flowchart of a process of launching one or more selected applications from a common management tool visually attached to an existing windows process window.

DETAILED DESCRIPTION

Figure 1:
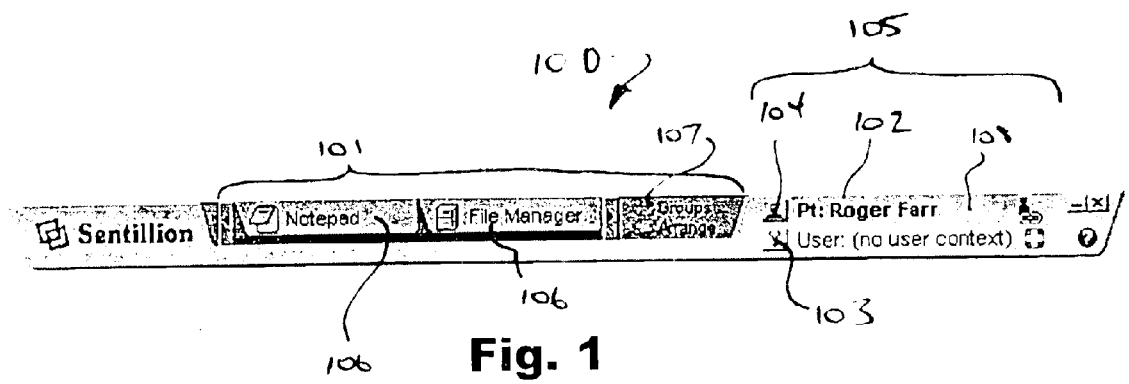
FIG. 1 is a screen shot of an embodiment of the invention showing elements of the user interface.

The present invention may be embodied in a software program, which executes under any one of several operating systems on a computer workstation. Operating systems under which the invention may be practiced include, but are not limited to, Windows 95, Windows 98, Windows 2000, Windows NT, Linux, UNIX, Mac OS and SUN OS. Preferably, the operating system and applications software in connection with which the present invention will be practiced includes a graphical type user interface. In preferred operating systems, such as the Windows systems or Mac OS, each application program process may interact with a user through a graphical interface element known as a window.

The exemplary embodiment of the invention is described in connection with the Windows 98 operating system. Some known methods of working with windows and messages in the operating system are referred to. In other operating systems, other known methods may be required or preferred. The exemplary embodiment is also described in connection with context management in the healthcare industry. Other forms of software integration in other industries can also be accomplished using the principles of the invention.

The present invention may be embodied in a software tool, which produces a user interface window (see FIG. 1, 100) that visually attaches itself to a lower edge of a process window having the focus and follows the movements of the lower edge of the process window. A process window is said to have the focus when the process controlling that window is the process that will actually receive user input as directed by the user via a mouse, keyboard or other known user input device. The status of having the focus is often indicated by the presence of a graphical element indicating an insertion point or cursor, or other indication within a user interface element of the window that input can be received. When the focus moves from one window to another, the user interface elements produced by embodiments of the invention automatically detach from the window formerly having the focus and reattach to the window now having the focus.

According to embodiments of the invention, as shown in FIG. 1, there is provided a software tool, which collects together in a single user interface element 101 a set of tools common to a unified overall task, such as healthcare management. Thus, through an embodiment of the present invention, one could access any of various clinical applications in a healthcare environment, without having to navigate through a series of folders, menus or windows as is commonly done in conventional windowing type operating systems.

According to embodiments of the present invention, there is a single user interface element 102 through which a user can change context information for plural, context-managed applications. For example, in the healthcare industry, a user may need to log into several clinical applications 103 or may need to change patient identification information 104 in several clinical applications. Changes would be made in one place, in a standardized format, and they would then propagate to all of the context managed clinical applications.

Finally, embodiments of the present invention provide a single point of user contact for displaying and delivering context related status information 105 regarding one or more context managed applications. For example, for each application available to a user, there can be an indication as to whether that particular application is context enabled, i.e., can be context managed, and whether that application is linked to the current context.

An embodiment of the present invention executing under the Windows 98 operating system is now described.

In order to attach to a process window, as described above, the embodiment of the invention intercepts certain windows messages communicated between processes using a technique known in the art as hooking and subclassing. Hooking and subclassing is described in greater detail below.

By visually attaching to the bottom of a process window, the user interface according to this embodiment of the invention, as shown in FIG. 1, is always available. The elements thereof are not hidden or obscured as they would be if contained in a folder, subfolder, menu or submenu, as conventionally done. However, the elements of the user interface according to this embodiment of the invention also remain unobstrusive. Unlike a conventional tool palette or tool bar, they do not obscure any currently used portion of the user's screen. In order to provide an attactive and instructive metaphor, the illustrated embodiment of the invention has the visual appearance of one or more tabs, attached to the bottom edge of the process window having the focus.

As described above, when the focus switches from one window to another, the visual user interface generated by the software program of this embodiment of the invention switches to the bottom of the window now having the focus. Should all of the windows available on screen be closed by the user or otherwise, the interface will attach to the bottom edge of the user's screen, so as to remain available.

Since the user interface elements created by this embodiment of the invention are contained within their own window, although they may have a special or unusual appearance, they can be given behaviors similar to any window created under the windows operating system. For example, the entire user interface element can be shrunk to a button on the task bar, like other applications, by clicking the proper control.

In one region 101 of the user interface element 100 created by this embodiment of the invention, there is provided a scrolling collection of application tabs 106. All of the applications useful at a particular workstation, including applications related to a particular overall mission of the workstation, can be installed to this portion of the user interface. By clicking on one of the tabs 106, an application is launchable, regardless of what other activity the workstation may be engaged in. Groups of applications used together can be defined and assigned to a single control accessible through a group button 107 so that a group of applications is launchable with one gesture. Launching single applications or groups of applications is performed by the user interface in a conventional manner, upon receipt of a message that the proper gesture has been performed. The above-described arrangement avoids having to search for applications hidden in folders, subfolders, menus and submenus, having to launch applications of a commonly used group one at a time and having to use awkward shortcut key sequences such as the alt-tab sequence used. Also, when a tab selected includes an application already running, the exemplary embodiment simply moves the focus to the existing instance of the application.

Context management functions are also centralized in the user interface element provided by this embodiment of the invention. User login is centralized. Therefore, a single user login format with a single user ID can be used. Users do not need to remember the various user login formats, which may be required of them for the various clinical applications in use. In order to avoid having to remember plural login formats, some users may elect to always login first through a particular context managed application. However, this application may not always be in use, thus creating extra steps for a user to locate and launch the application. Through the user interface of the illustrated embodiment of the invention, the user simply clicks on the user ID control to launch the particular context managed application and enter their universal user identification information into the application. In the exemplary embodiment, this control may be configured to launch a different particular context managed application for different users. The universal user identification information is mapped to the user IDs used by the various context managed clinical applications and the context of all context-managed applications adjusted accordingly. Common administration of user login information is described in detail in U.S. patent application Ser. No. 09/545,396, referred to above.

In similar fashion to user login, patient context is also centralized, and therefore standardized. Therefore, a single patient selection format with a single patient ID can be used. Users do not need to remember the various patient selection formats, which may be required of them for the various clinical applications in use. In order to avoid having to remember plural patient selection formats, some users may elect to always select a patient first through a particular context managed application. However, this application may not always be in use, thus creating extra steps for a user to locate and launch the application. Through the user interface of the illustrated embodiment of the invention, the user simply clicks on the patient ID control to launch the particular context managed application and enters their universal user identification information into the application. In the embodiment of this invention the specific application that is launched when this control is clicked may be configured so that it is not necessarily the same application for all users. The universal patient identification information is mapped to the patient IDs used by the various context managed clinical applications and the context of all context-managed applications adjusted accordingly. Common administration of user login information is described in detail in U.S. patent application Ser. No. 09/545,396, referred to above.

All conventional context management status information in accordance with context management standards is shown in one place, the user interface 100 provided by this embodiment of the invention. Context enablement status can be obtained by activating a control on tabs 106. Moreover, this embodiment of the invention can present instant messages, which are tied to the current context. For example, a message entered by one user about a particular patient can instantly show up on the screen of any other user whose context has that patient selected or who subsequently selects that patient as part of their context. In the exemplary embodiment, the presence of an instant message is indicated by an icon appearing adjacent the patient name in space 108. The icon in space 108 is a control to access the message.

The software program of the illustrated embodiment of the present invention consists of two components. One component is an executable program. The other component is a dynamic linked library (DLL).

The executable program is a Windows program, which can be launched and run, for example, by the Windows Run . . . command. Conveniently, the executable program can be launched on Windows startup by dropping a shortcut to the executable program into the Startup folder of the Windows user profile. The executable program is invoked to launch operation of the user interface tool, which generates the visual element of the user interface and which performs the actions requested by user interaction with the user interface. The executable program also sets the hooking DLL, as described below. The DLL contains all of the program code required to manipulate the location of the visual elements of the user interface to give it the appearance of being part of another process' window.

Hooking and subclassing is described in detail in Advanced Windows, pages 905–911. In essence, messages that would have been passed to a given process are passed first to the hook DLL, which has a function defined to handle the messages. By intercepting window control messages, etc., this embodiment of the present invention can determine where and when to draw the user interface window. It can also determine when the window moves, changes size or loses the focus. Thus, by hooking and subclassing, the program according to this embodiment of the invention gains complete control over its own display. Although hooking and subclassing is well known, and has been used, for example, in the Spy program to intercept and examine windows messages, this type of processing has not been used to create the window of the present invention that attaches to another process' window.

The hooking and subclassing process is illustrated in FIG. 2. In step 201, the user interface tool executable, referred to as Launchpad, is started and the hook set. An application is launched, or may be already running, step 202. Windows then loads the hook DLL into the application process, step 203. In step 204, Launchpad decides whether, according to its configuration, the application should be added. If not, the hook DLL is unloaded from the process, step 207. Otherwise, step 205, the windows in the application are subclassed. Finally, the subclass function monitors windows messages to move the Launchpad user interface elements to appropriate locations, step 206. The process of changing or entering context information, in this case the patient ID, is illustrated in FIG. 3. First, the patient icon (FIG. 1, 104) is clicked, step 301. The application configured for entry of the patient ID is then launched, step 302. In step 303, the application sets the context in the context manager. Finally, the new patient ID is displayed (FIG. 1, 102), step 304.

FIG. 4 illustrates the process of launching an application using an embodiment of the invention. First, step 401, a user reelects an application tab. If the configuration of the application such that a new instance is always started, step 402. If so, a new instance is started, step 403. In step 404, processing continues with step 203 of FIG. 2. If, in step 402, configuration is set not to launch a new instance, a check for an existing instance is made, step 405. If there is no existing instance, processing continues at step 403. Otherwise, a window of the instance is brought to the front and the focus set in that window, step 406.

The present invention has now been described in connection with a number of specific embodiments thereof. However, numerous modifications, which are contemplated as falling within the scope of the present invention, should now be apparent to those skilled in the art. Therefore, it is intended that the scope of the present invention be limited only by the scope of the claims appended hereto.

What is claimed is:

1. A software program stored on a computer-readable medium, the software program comprising instructions for execution on a computer comprising a display, at least one input device, a plurality of application programs and an operating system that, when two or more of the plurality of application programs are executing simultaneously, moves a focus among the simultaneously executing application programs so that only one of the simultaneously executing application programs has the focus and receives input from the at least one input device at a time, the plurality of application programs sharing a context which is managed in accordance with a Clinical Context Object Workgroup (CCOW) standard, the plurality of application programs including a first application program and a second application program, the display presenting first and second user interface elements associated with the respective first and second application programs, the instructions when executed, performing a sequence of steps, comprising:

identifying that the first application program has the focus;

in response to identifying that the first application program has the focus, visually attaching to the first user interface element of the first application program a user interface element of the software program, the user interface element of the software program enabling a user to change information defining the context shared by the plurality of applications, the information identifying a patient and a user;

moving and resizing, on the display, the user interface element of the software program together with the first user interface element while the first application program has the focus, so the user interface element of the software program and the first user interface element of the first application program together give a visual impression on the display of one user interface;

identifying that the focus has switched from the first application program to the second application program; and in response to identifying that the focus has switched from the first application program to the second application program, detaching the user interface element of the software program from the first user interface element of the first application program and attaching the user interface element of the software program to the second user interface element of the second application program.

2. The software program of claim 1, wherein the sequence of steps further comprises:

displaying a control for a user to enter context information used by the plurality of application programs.

3. The software program of claim 1, wherein the sequence of steps further comprises:

displaying a control which when activated displays context information.

4. The software program of claim 1, wherein the sequence of steps further comprises:

displaying a scrollable set of tabs by means of which at least one of the plurality of applications programs can be launched.

5. The software program of claim 1, wherein the sequence of steps further comprises:

displaying a control which when activated, invokes an instantiation of a web browser pointed to a predetermined web site.

6. The software program of claim 5, wherein the sequence of steps further comprises:

defining the predetermined web site.

7. The software program of claim 5, wherein the sequence of steps further comprises:

defining a visual image for the control which invokes the web browser including a corporate logo.

8. The software program of claim 1, wherein the sequence of steps further comprises:

defining controls on the user interface element of the software program which are dependent on an identified user.

9. The software program of claim 8, wherein the step of defining controls further comprises:

displaying a scrollable set of tabs representing those application programs, which, of the plurality of applications programs, the identified user has permission to launch.

10. The software program of claim 8, wherein the step of defining controls further comprises:

displaying a set of controls defined for the identified user at a particular workstation.

11. The software program of claim 1, wherein the sequence of steps further comprises steps of:

moving, and resizing, on the display, the user interface element of the software program together with the second user interface element while the second application program has the focus, so the user interface element of the software program and the second user interface element of the second application program together give a visual impression on the display of one user interface.

12. A method of controlling a computer comprising a display, at least one input device, a plurality of application programs, and an operating system that, when two or more of the plurality of applications are executing simultaneously, moves a focus among the simultaneously executing application programs so that only one of the simultaneously executing application programs has the focus and receives input from the at least one input device at a time, the plurality of application programs sharing a context which is managed in accordance with a Clinical Context Object Workgroup (CCOW) standard, the plurality of application programs including a first application program and a second application program, the display presenting first and second user interface elements associated with the respective first and second application programs the method comprising computer-implemented steps of:

identifying that the first application program has the focus;

in response to identifying that the first application program has the focus, visually attaching to the first user interface element of the first application program a user interface element of a software program, the user interface element of the software program enabling a user to change information defining the context shared by the plurality of applications, the information identifying a patient and a user;

moving and resizing, on the display, the user interface element of the software program together with the first user interface element while the first application program has the focus, so the user interface element of the software program and the first user interface element of the first application program having the focus together give a visual impression on the display of one user interface;

identifying that the focus has switched from the first application program to the second application program, and in response to the step of identifying that the focus has switched from the first application program to the second application program, detaching the user interface element of the software program from the first user interface element of the first application program and attaching the user interface element of the software program to the second user interface element of the second application program.

13. The method of claim 12, further comprising:

displaying a control for a user to enter context information used by the plurality of application programs.

14. The method of claim 12, further comprising:

displaying a control which when activated displays context information.

15. The method of claim 12, further comprising:

displaying a scrollable set of tabs by means of which at least one of the plurality of applications programs can be launched.

16. The method of claim 12, further comprising:

displaying a control which when activated, invokes an instantiation of a web browser pointed to a predetermined web site.

17. The method of claim 16, further comprising:

defining the predetermined web site.

18. The method of claim 16, further comprising:

defining a visual image for the control which invokes the web browser including a corporate logo.

19. The method of claim 12, further comprising:

defining controls on the user interface element of the software program which are dependent on an identified user.

20. The method of claim 19, wherein the step of defining controls further comprises:

displaying a scrollable set of tabs representing those application programs, which, of the plurality of applications programs, the identified user has permission to launch.

21. The method of claim 19, wherein the step of defining controls further comprises:

displaying a set of controls defined for the identified user at a particular workstation.

22. The method of claim 12, wherein the computer-implemented steps are performed by the software program.

23. The method of claim 12, wherein the method further comprises computer-implemented steps of:

moving and resizing, on the display, the user interface element of the software program together with the second user interface element while the second application program has the focus, so the user interface element of the software program and the second user interface element of the second application program together give a visual impression on the display of one user interface.

* * * * *